United States Patent

DeLuke

(10) Patent No.: US 6,837,246 B1
(45) Date of Patent: Jan. 4, 2005

(54) TONGUE-AIRWAY APPLIANCE

(76) Inventor: Anthony G. DeLuke, 5043 Forest Rd., Lewiston, NY (US) 14092

(*) Notice: Subject to any disclaimer, the term of this patent is extended or adjusted under 35 U.S.C. 154(b) by 0 days.

(21) Appl. No.: 10/244,353

(22) Filed: Sep. 16, 2002

Related U.S. Application Data

(60) Provisional application No. 60/322,101, filed on Sep. 14, 2001.

(51) Int. Cl.$^7$ ................................................. A61C 5/14
(52) U.S. Cl. ........................ 128/860; 128/861; 128/862
(58) Field of Search ................................ 128/846, 848, 128/859–862; 433/6; 602/902

(56) References Cited

U.S. PATENT DOCUMENTS 3,478,742 A  *  11/1969  Bohlmann ................... 128/860
3,871,370 A  *  3/1975   McDonald ................... 128/860
4,718,662 A  *  1/1988   North ......................... 128/136
RE33,442 E  *  11/1990  George ........................... 433/6
5,092,346 A  *  3/1992   Hays et al. ................. 128/848
5,682,903 A  *  11/1997  Meade ......................... 128/848

* cited by examiner

Primary Examiner—Michael A. Brown
(74) Attorney, Agent, or Firm—Hodgson Russ LLP

(57) ABSTRACT

An intra-oral appliance in the form of a tongue-airway functional appliance which restores/encourages training of the tongue, which encourages patients to breathe through the nose, and which can serve as a diagnostic aid or test device to access a patient's problems. The appliance includes a body of plastic material having an arcuate-shaped portion along which is defined a recess for receiving teeth of a dental arch of a patient, preferably the upper arch. The appliance further includes a curved platform or extension from the body running from the area of the lingual gingival margin of all teeth inferiorly (toward the mandible) forming a "U" or cup-shaped portion or sling which passes under the tongue laterally and anterior to posterior. In another embodiment, nubs or projections are provided on the walls of the teeth-receiving recess for enhancing retention of the appliance.

16 Claims, 3 Drawing Sheets

TONGUE-AIRWAY APPLIANCE

CROSS REFERENCE TO A RELATED APPLICATION

Applicant hereby claims priority based on U.S. Provisional Patent Application No. 60/322,101 filed Sep. 14, 2001 and entitled "Tongue-Airway Appliance."

BACKGROUND OF THE INVENTION

This invention relates to the art of intra-oral appliances, and more particularly to a new and improved tongue-airway functional appliance.

A number of therapeutic and diagnostic considerations are associated with functioning of the tongue. Therapeutic considerations are related to the need for restoration and/or encouragement of tongue training. Such training can be needed due to a variety of pre-existing problems. One is thumb sucking habit. Another is neurological damage secondary to trauma or disease and associated surgery (stroke). Still another is genetically predisposed physiological abnormality. Iatrogenic problems (dentist caused) also create a need for such training. These involve a change in normal function secondary to prolonged wearing of a maxillary appliance which blocks normal positioning of the tongue against the palate. A further problem is blocked nasal airway causing a habitual abnormal "low-tongue" posture. From a therapeutic standpoint, such training advantageously encourages patients to breathe through their nose. It "retains" the mouth breathing habit. Conditions associated with the condition of habitual mouth breathing include increased tooth decay, periodontal disease, reduced blood oxygen levels (with associated problems), and abnormal facial growth.

Diagnostic considerations associated with functioning of the tongue involve verification of intensity or severity of a swallow abnormality and verification of nasal obstruction.

SUMMARY OF THE INVENTION

The present invention provides an intra-oral appliance in the form of a tongue-airway functional appliance which restores/encourages training of the tongue, which encourages patients to breathe through the nose, and which can serve as a diagnostic aid or test device to access a patient's problems. The appliance includes a body of plastic material having an arcuate-shaped portion along which is defined a recess for receiving teeth of a dental arch of a patient, preferably the upper arch. The appliance further includes a curved platform or extension from the body running from the area of the lingual gingival margin of all teeth inferiorly (toward the mandible) forming a "U" or cup-shaped portion or sling which passes under the tongue laterally and anterior to posterior. In another embodiment, extensions are provided on the walls of the teeth-receiving recess for enhancing retention of the appliance.

The following detailed description, when read in conjunction with the accompanying drawing, is in such full, clear, concise and exact terms as to enable any person skilled in the art to which it pertains, or with which it is most nearly connected, to make and use the invention. The foregoing and additional advantages and characterizing features of the present invention will become clearly apparent upon a reading of the ensuing detailed description together with the included drawing.

DETAILED DESCRIPTION OF THE INVENTION

The intra-oral appliance of the present invention is a tongue-airway functional appliance serving as a tongue guide. The appliance functions in the following ways. It restores/encourages training of the tongue which can be needed due to a variety of pre-existing problems discussed hereinabove. The appliance also encourages patients to breathe through the nose thereby retraining the mouth breathing habit. Such retraining of the habitual resting position of the tongue as well as the active tongue positioning occurring during the swallow of saliva can be complemented by speech therapy-like exercises.

The appliance also can serve as a diagnostic aid or test device to access the patient's problems. Intensity or severity of a swallow abnormality is quickly and easily verified when the patient attempts to wear the appliance. Additionally, nasal obstruction is easily verified. Patients with significant obstruction cannot wear this appliance whatsoever. Appropriate referral can be made to ear, nose, and throat specialists with reliability when this situation is confronted.

Figure 1:
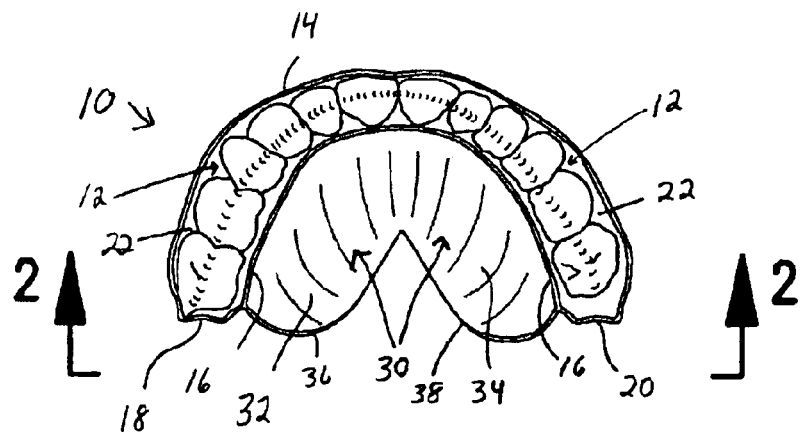
FIG. 1 is a top plan view of the tongue-airway appliance according to the present invention.
Figure 2:
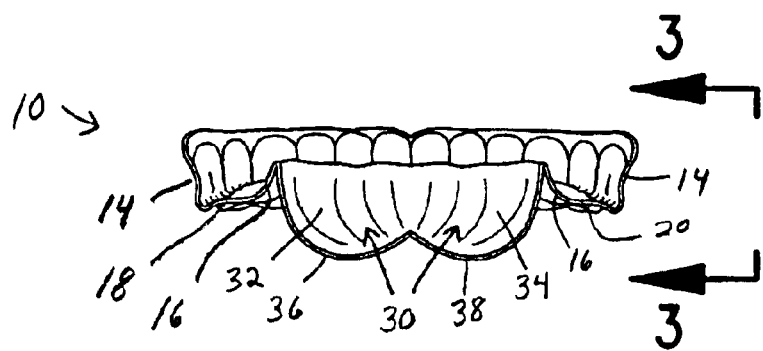
FIG. 2 is an end elevational view taken about on lines 2—2 in FIG. 1.
Figure 3:
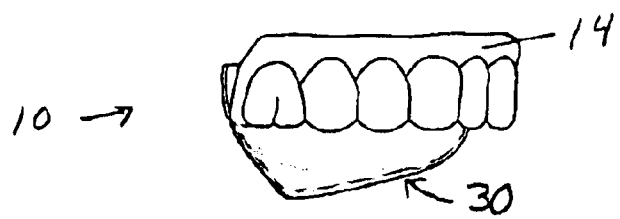
FIG. 3 is a side elevational view taken about on lines 3—3 in FIG. 2.

Referring now to FIGS. 1-3, the appliance 10 of the present invention comprises a body of plastic material having a substantially arcuate-shaped portion along which is defined a recess or channel 12 to receive the teeth of a dental arch of a patient. In the device illustrated in FIGS. 1-3 the dental arch is the upper arch of the patient. The channel 12 is defined by an outer, thin wall 14 which extends along a substantially arcuate path and an inner, thin wall 16 which also extends along a substantially arcuate path. In the appliance shown, walls 14 and 16 are of the same thickness. Walls 14 and 16 terminate at ends 18 and 20 at the rear of the appliance. The walls 14, 16 extend from a substantially arcuate bottom wall 22 which, in the device shown, is of the same thickness as walls 14 and 16. The appliance 10 further comprises a shaped platform 30 from the body running from the area of the lingual gingival margin of all teeth inferiorly (toward the mandible) forming a substantially "U" shaped or cup-shaped portion (sling) which passes under the tongue laterally, i.e. from right to left or vice-versa, and anterior to posterior. Platform 30 is shaped to receive and support the front portion of a patient's tongue. Platform 30 includes two, semi-cup-shaped halves 32 and 34 which are separated by an open region extending approximately half-way along the longitudinal, i.e., anterior to posterior, dimension of platform 30. The semi-cup-shaped halves 32, 34 conform to the shape of the lower surface of the front of a patient's tongue. The open region is located between the peripheral edges 36 and 38 of the semi-cup-shaped halves 32 and 34, respectively. The open space promotes comfort and mobility for the tongue and provides space for lingual frenum. In the appliance shown, the thickness of platform 30 is the same as that of walls 14, 16 and 22.

The appliance can be made of medical grade silicone or a similar material. It would be made in a number of sizes (possibly 4–6). The sizes correspond to young children thru adults. The various sizes would correspond to increasing width and length of the dental arches.

Figure 4:
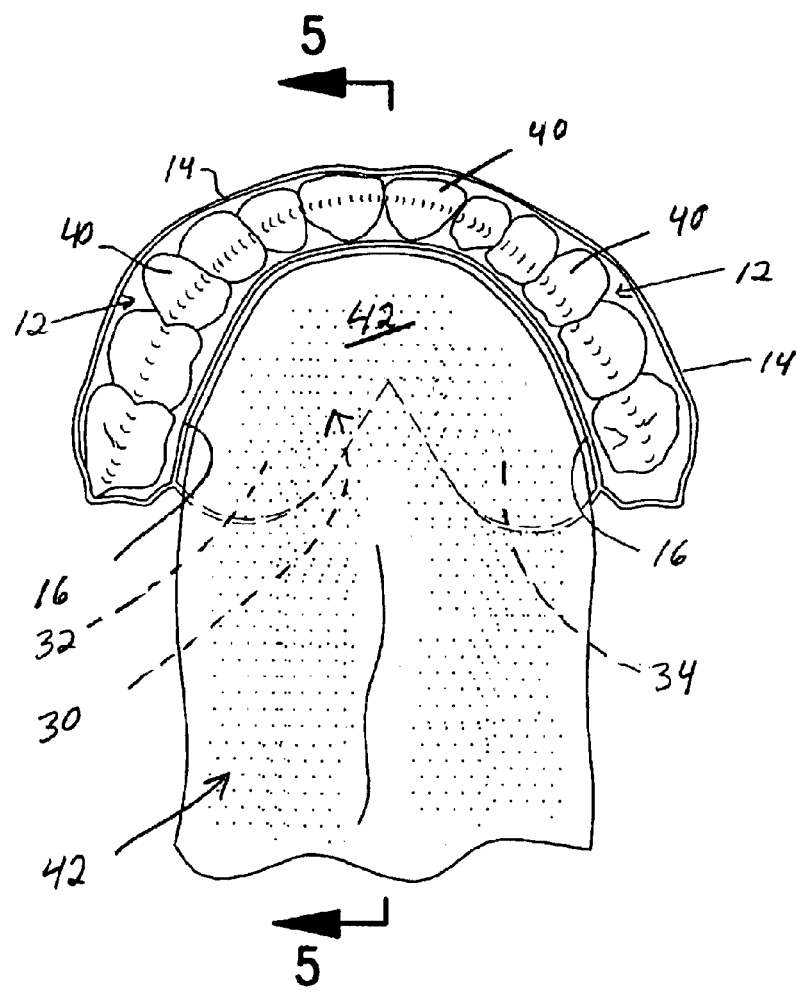
FIG. 4 is top plan view of the appliance of FIGS. 1-3 positioned in a patient's mouth and taken about on lines 4—4 in FIG. 5.
Figure 5:
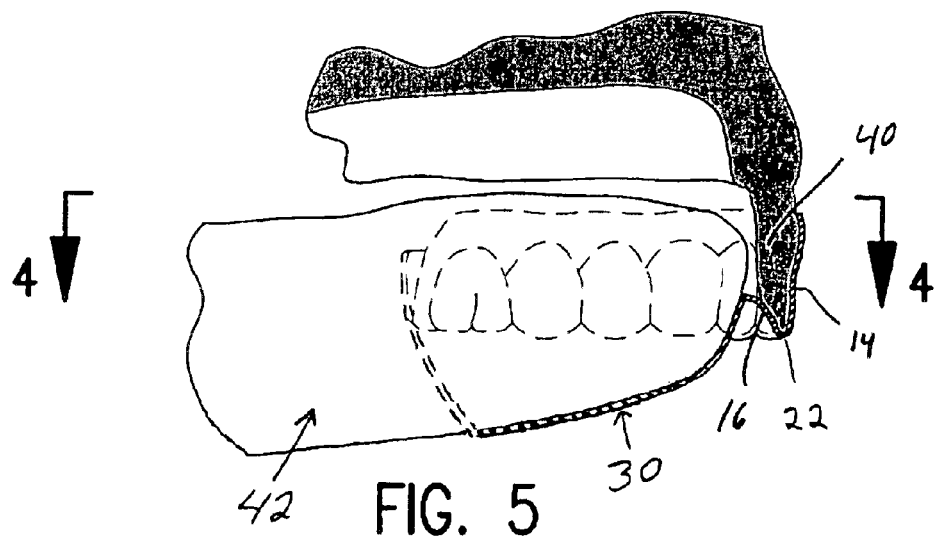
FIG. 5 is a fragmentary longitudinal sectional view taken about on lines 4—4 in FIG. 4.

FIGS. 4 and 5 show the appliance 10 positioned in a patient's mouth with teeth 40 of the upper arch received in channel 12 between walls 14 and 16 and with the front or tip region of the patient's tongue supported by platform 30.

The retention of the appliance is accomplished both passively and actively. Patients are instructed to bite onto the appliance consistently, and this biting force can be very light. This and the soft material interface between the teeth which the patient is biting onto assures their comfort.

Figure 6:
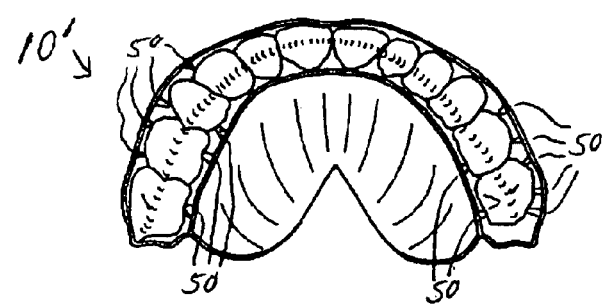
FIG. 6 is a top plan view of an appliance according to another embodiment of the present invention.

In accordance with another embodiment of the present invention, the appliance 10' can be provided extensions, a few of which are shown at 50 in FIG. 6, which wrap around and pass gingival to the upper teeth from molar to molar. The extensions 50 project inwardly from walls 14 and 16 as shown. These are fully extended into both the labial and buccal vestibules. These extensions 50 would taper and have a slight curvature following the natural contours of the alveolar bone superior to the teeth. These extensions 50 will create retention by the passive musculature tug or tension pulling inward trapping the soft appliance extensions between the teeth, alveolar bone superior to the clinical crowns, and lip or cheek muscles.

By way of example, in an illustrative appliance, cove-like rows of projections 50 approximately 1½ mm diameter by 3 mm in height in rows separated by 2 mm will project perpendicular to the inside surface of the tooth channel of the appliance and are directed at the teeth and gingiva. These projections 50 allow for a generalized, comfort fit which would adapt the individual variations of tooth size and shape. The comfort fit "nubs" or projections 50 will allow manufacture of three or four sizes to accommodate all patients, adults and children. An additional advantage of the embodiment of FIG. 6 is that the appliance can be worn over orthodontic braces.

For the embodiment of FIGS. 1-5, standard models would be fabricated corresponding to each size. The models would have progressively greater width and length of the area corresponding to growing maxillary arch size. These models would also have a tongue sculpted to completely fill the space available corresponding to the height of the palate as well as the length and width of the alveolar arch.

Two alternative fabrication techniques could be considered. A Biostar machine would form a soft sheet material over the "ease" models of the patient's upper arch. In particular, one half of the forming component of the Bipolar machine would receive the dental model of the patient's arch. The other, mating half of the forming component of the Bipolar machine can be provided with an insert of plaster, wax or other appropriate material to serve as a mold component to shape and form the tongue-supporting platform. For a more detailed description of the Bipolar machine and its method of operation, reference may be made to U.S. Pat. No. 3,768,164, the disclosure of which is incorporated herein by reference. A suitable thermoplastic material is 2 mm thickness mouth guard material commercially available from Great Lakes Orthodontics Ltd. under the designations GL2250 and GL2251. After the thermoforming operation is completed, an initial trimming would be done by the lab technician with scissors to standard templates. Relief for the lingual freon as well as other muscular-tissue areas in the buccal and labial vestibules would be completed. Final trimming may occasionally be done by the dentist. The foregoing method results in an appliance of unitary or integral structure. That is the walls 14, 16 and 22 together with the platform 30 including the two cup-shaped halves 32 and 34 are all formed from the same single sheet of thermoplastic material. An alternative fabrication technique could be to create a mold for each size and "injection-mold" the appliance out of a medical grade silicone. For the appliance of FIG. 6, manufacture would be by way of a latex or silicone injection molding process.

While embodiments of the present invention have been described in detail, that is for the purpose of illustration, not limitation.

What is claimed is:

1. An oral appliance for training of a patient's tongue comprising:
   a) a body of plastic material having a substantially arcuate-shaped portion along which is defined a recess to receive teeth of a dental arch of a patient, the recess being defined by a pair of spaced-apart walls extending from a bottom wall disposed in a plane; and
   b) a platform extending from the body for supporting the patient's tongue and shaped to accommodate the lower surface of the front portion of the tongue, the platform extending from the area of the lingual gingival margin of all teeth toward the mandible and passing laterally under the tongue and in a direction from an anterior location on the appliance, the platform being located in spaced relation below the plane of the recess bottom wall, the platform including two semi-cup-shaped portions separated by a region extending longitudinally of the appliance.

2. An appliance according to claim 1, wherein the recess is oriented in the body to receive teeth of an upper dental arch of a patient.

3. An appliance according to claim 1, wherein the plastic material is a thermoplastic material.

4. An appliance according to claim 1, further including projections in the recess and formed in the body for contacting the patient's teeth.

5. An appliance according to claim 1, further including projections extending inwardly from the walls for contacting the patient's teeth.

6. An appliance according to claim 1, wherein the substantially arcuate-shaped portion and the platform are integral parts of the body of plastic material.

7. An oral appliance for training of a patient's tongue comprising:
   a) a body of plastic material having a substantially arcuate-shaped portion along which is defined a channel to receive teeth of the upper arch of a patient; and
   b) a substantially cup-shaped platform extending from the body for supporting the patient's tongue and accommodating the lower surface of the front portion of the tongue, the platform including two semi-cup-shaped portions separated by a region extending longitudinally of the appliance, the two portions being substantially concave for conforming to and receiving the lower surface of the front portion of a patient's tongue.

8. An appliance according to claim 7, wherein the platform extends from the area of the lingual gingival margin of all teeth toward the mandible and passes laterally under the tongue and in a direction from an anterior location on the appliance to a posterior location on the appliance.

9. An appliance according to claim 7, further including projections within the channel and formed in the body for contacting the patient's teeth.

10. A method of making an oral appliance for training appliance comprising:

a) providing a model of the upper dental arch of a patient;

b) providing a mold component to define a substantially cup-shaped platform within the dental arch;

c) providing a sheet of thermoplastic material;

d) thermoforming the plastic material on the teeth of the dental arch and on the mold component; and e) trimming the plastic material to define a substantially cup-shaped tongue-supporting platform extending from a substantially arcuate-shaped tooth-receiving channel portion of the appliance.

11. A method according to claim 10, wherein the thermoforming and the trimming provide a platform extending from the area of the lingual gingival margin of all teeth toward the mandible and passing laterally under the tongue and in a direction from an anterior location on the appliance to a posterior location on the appliance.

12. A method according to claim 10, wherein the mold component defines two semi-cup-shaped platform portions.

13. A method according to claim 12, wherein the trimming provides a separation located between the two semi-cup-shaped portions of the platform and extending longitudinally of the appliance.

14. An oral appliance for training of a patient's tongue comprising:

a) a body of plastic material having a substantially arcuate-shaped portion along which a pair of spaced-apart walls extend to define a recess to receive teeth of a dental arch of a patient, the walls having inner surfaces shaped to conform to surfaces of the patient's teeth;

b) a platform extending from the body for supporting the patient's tongue and shaped to accommodate the lower surface of the front portion of the tongue, the platform including two semi-cup-shaped portions separated by a region extending longitudinally of the appliance; and c) at least one of the walls being provided with a plurality of inwardly projecting extensions for creating retention and adapting to patient variations in tooth size and shape.

15. An appliance according to claim 14, wherein both walls are provided with the extensions.

16. An appliance according to claim 14, wherein the recess is oriented in the body to receive teeth of an upper dental arch of a patient.

* * * * *